US012649705B2

(12) United States Patent
List et al.

(10) Patent No.: US 12,649,705 B2
(45) Date of Patent: Jun. 9, 2026

(54) PROCESS FOR THE ASYMMETRIC SYNTHESIS OF ISOPIPERITENOL

(71) Applicant: Studiengesellschaft Kohle gGmbH, Muelheim (DE)

(72) Inventors: Benjamin List, Muelheim an der Ruhr (DE); Joyce Grimm, Muelheim (DE); Hui Zhou, Muelheim an der Ruhr (DE); Luping Liu, San Diego, CA (US); Alexander Zwerschke, Rhede (DE)

(73) Assignee: Studiengesellschaft Kohle gGmbH, Muelheim (DE)

( * ) Notice: Subject to any disclaimer, the term of this patent is extended or adjusted under 35 U.S.C. 154(b) by 529 days.

(21) Appl. No.: 18/259,806

(22) PCT Filed: Dec. 30, 2021

(86) PCT No.: PCT/EP2021/087886
§ 371 (c)(1),
(2) Date: Jun. 29, 2023

(87) PCT Pub. No.: WO2022/144436
PCT Pub. Date: Jul. 7, 2022

(65) Prior Publication Data

US 2024/0083829 A1 Mar. 14, 2024

(30) Foreign Application Priority Data

Dec. 31, 2020 (EP) .................................... 20217996

(51) Int. Cl.

| | |
|---|---|
| ***C07C 29/145*** | (2006.01) |
| ***B01J 31/02*** | (2006.01) |
| *C07C 29/17* | (2006.01) |
| *C07C 37/16* | (2006.01) |
| *C07D 311/80* | (2006.01) |

(52) U.S. Cl.
CPC ......... *C07C 29/145* (2013.01); *B01J 31/0265* (2013.01); *C07C 29/172* (2013.01); *C07C 37/16* (2013.01); *C07C 2601/16* (2017.05); *C07D 311/80* (2013.01)

(58) Field of Classification Search
None
See application file for complete search history.

(56) References Cited

U.S. PATENT DOCUMENTS

| | | | |
|---|---|---|---|
| 11,084,834 | B2 | 8/2021 | List et al. |
| 2006/0155153 | A1 | 7/2006 | Selifonov |

FOREIGN PATENT DOCUMENTS

| | | | |
|---|---|---|---|
| DE | 2305629 C2 | 6/1982 |
| WO | 2004/013339 A1 | 2/2004 |
| WO | 2017/037141 A1 | 3/2017 |

*Primary Examiner* — Clinton A Brooks
(74) *Attorney, Agent, or Firm* — Norris Mclaughlin, PA

(57) ABSTRACT

The present invention refers to a process for the asymmetric synthesis of isopiperitenol and successor compounds.

13 Claims, 1 Drawing Sheet

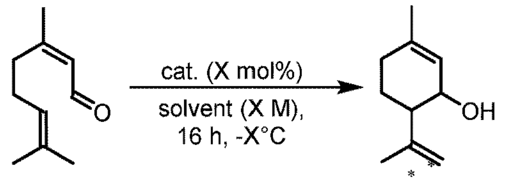

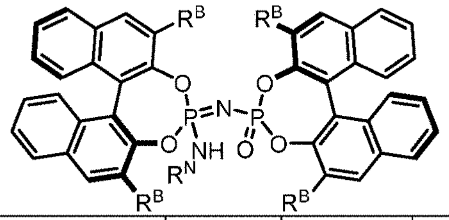

| entry | $R^B$ | $R^N$ | solvent | T [°C] | Cat. Loading | concentration | Yield [%] | conv. [%] | d.r. | e.r. (trans) | e.r. (cis) |
|---|---|---|---|---|---|---|---|---|---|---|---|
| 1 | 4-$SF_5$-Ph | $SO_2$-$C_4F_9$ | $CH_2Cl_2$ | -40 | 5mol% | 0.005M | 62 | 76 | 18:1 | 50.5:49.5 | 55.5:44.5 |
| 2 | 4-$CF_3$-Ph | $SO_2$-$CF_3$ | $CH_2Cl_2$ | -40 | 5mol% | 0.005M | 35 | 36 | 16:1 | 48:52 | 42:58 |
| 3 | 3-$CF_3$-Ph | $SO_2$-$CF_3$ | $CH_2Cl_2$ | -40 | 5mol% | 0.005M | 23 | 24 | 10:1 | 56.5:43.5 | 49:51 |
| 4 | 3,5-$(CF_3)_2$-Ph | $SO_2$-$CF_3$ | $CH_2Cl_2$ | -40 | 5mol% | 0.005M | 21 | 22 | 8:1 | 52:48 | 43:57 |
| 5 | 6-iPrF-naphth-2-yl | $SO_2$-$CF_3$ | $CH_2Cl_2$ | -40 | 5mol% | 0.005M | 49 | 52 | >20:1 | 85.5:14.5 | 44:56 |
| 6 | 6-F-naphth-2-yl | $SO_2$-$CF_3$ | $CH_2Cl_2$ | -40 | 5mol% | 0.005M | 20 | 20 | 17:1 | 79:21 | 57.5:42.5 |
| 7 | 4-$CF_3$-Ph | $SO_2$-$C_4F_9$ | $CH_2Cl_2$ | -40 | 5mol% | 0.005M | 32 | 34 | 14:1 | 51:49 | 46:54 |
| 8 | 3-Cl-4-$CF_3$-Ph | $SO_2$-$CF_3$ | $CH_2Cl_2$ | -40 | 5mol% | 0.005M | 39 | 58 | 13:1 | 49.5:50.5 | 39:61 |
| 9 | 6-PrF-naphth-2-yl | $SO_2$-$CF_3$ | $CH_2Cl_2$ | -40 | 5mol% | 0.005M | 42 | 44 | 16:1 | 80:20 | 46:54 |
| 10 | 6-HexF-naphth-2-yl | $SO_2$-$CF_3$ | $CH_2Cl_2$ | -40 | 5mol% | 0.005M | 28 | 45 | 17:1 | 76:24 | 52:48 |
| 11 | 7-iPrF-naphth-2-yl | $SO_2$-$CF_3$ | $CH_2Cl_2$ | -40 | 5mol% | 0.005M | 22 | 44 | 8:1 | 66:34 | 40:60 |
| 12 | Naphth-2-yl$_F$ | $SO_2$-$CF_3$ | $CH_2Cl_2$ | -40 | 5mol% | 0.005M | 70 | 71 | >20:1 | 0.7:99.3 | 71.5:28.5 |
| 13 | Naphth-2-yl$_F$ | $SO_2$-$CF_2H$ | $CH_2Cl_2$ | -40 | 5mol% | 0.005M | 15 | 20 | 9:1 | 3:97 | 61:39 |
| 14 | Naphth-2-yl$_F$ | $SO_2$-$C_2F_5$ | $CH_2Cl_2$ | -40 | 5mol% | 0.005M | 65 | 87 | >20:1 | 0.7:99.3 | 67:33 |
| 15 | Naphth-2-yl$_F$ | $SO_2$-$C_4F_9$ | $CH_2Cl_2$ | -40 | 5mol% | 0.005M | 61 | 84 | 20:1 | 1:99 | 68.5:31.5 |
| 16 | Naphth-2-yl$_F$ | $SO_2$-$C_6F_5$ | $CH_2Cl_2$ | -40 | 5mol% | 0.005M | 12 | 19 | - | 17.5:81.5 | 88:12 |
| 17 | Naphth-2-yl$_F$ | $SO_2$-$CF_3$ | $CH_2Cl_2$ | -40 | 10mol% | 0.005M | 77 | 80 | 25:1 | 0.6:99.4 | 70:30 |
| 18 | 3-F-4-$CF_3$-Ph | $SO_2$-$CF_3$ | $CH_2Cl_2$ | -40 | 5mol% | 0.005M | 31 | 44 | 10:1 | 40:60 | 33:67 |
| 19 | 4-Tf-Ph | $SO_2$-$CF_3$ | $CH_2Cl_2$ | -40 | 5mol% | 0.005M | 25 | 45 | 16:1 | 36:64 | 43:57 |
| 20 | 3,5-$(OMe)_2$-Ph | $SO_2$-$CF_3$ | $CH_2Cl_2$ | -40 | 5mol% | 0.005M | 12 | 17 | 9:1 | 92:8 | 31:69 |
| 21 | Naphth-2-yl$_F$ – H8-BINOL | $SO_2$-$CF_3$ | $CH_2Cl_2$ | -40 | 5mol% | 0.005M | 6 | 14 | 20:1 | 12:88 | 62:38 |
| 22 | Naphth-2-yl$_F$ – 6,6'-Me-BINOL | $SO_2$-$CF_3$ | $CH_2Cl_2$ | -40 | 5mol% | 0.005M | 22 | 39 | 14:1 | 0.6:99.4 | 77.5:22.5 |
| 23 | Naphth-2-yl$_F$ – 6,6'-iPr$_F$-BINOL | $SO_2$-$CF_3$ | $CH_2Cl_2$ | -40 | 5mol% | 0.005M | 52 | 80 | 17:1 | 1.5:98.5 | 53:47 |
| 24 | Naphth-2-yl$_F$ | $SO_2$-$CF_3$ | pentane | 0 | 5mol% | 0.005M | 68 | 94 | 11:1 | 1.5:98.5 | 71:29 |
| 25 | Naphth-2-yl$_F$ | $SO_2$-$CF_3$ | pentane | 0 | 2.5mol% | 0.1M | 48 | 96 | 8:1 | 4:96 | 61:39 |

PROCESS FOR THE ASYMMETRIC SYNTHESIS OF ISOPIPERITENOL

This application is a 371 of International Patent Application No. PCT/EP2021/087886, filed Dec. 30, 2021, which claims priority of European Patent Application No. 20217996.6, filed Dec. 31, 2020, the disclosure of which patent applications are hereby incorporated herein by reference.

The present invention refers to a process for the asymmetric synthesis of isopiperitenol and successor compounds.

Isopiperitenol is an important precursor compound used in the synthesis of industrially important substances such as menthol, CBD, THC and other resorcinol-derived natural products. One of the important processes for the industrial synthesis of menthol stereoisomers in the prior art is the so-called BASF process.

Said menthol process of BASF includes two hydrogenation steps starting from Geranial or Neral. The first asymmetric C═C-bond hydrogenation is therefore being used to introduce the stereocenter at the β-position of citronellal as shown in the following scheme. Cyclization of citronellal in presence of a Lewis- or Brønsted acid yields isopulegol which upon further C═C-bond hydrogenation gives rise to a reaction mixture containing several menthol stereoisomers.

Using modified citral derivatives or other monoterpenes as starting materials (Marshall et al., J. Org. Chem. 1988, 53, 4108; Nakamura et al., Bull. Chem. Soc. Jpn. 1992, 65, 929-931; Semikolenov et al. Kinet. Catal. Lett. 2004, 82, 165;

Reduction of cyclic ketones (Tetrahedron: Asymmetry 2007, 17, 717, Rao)

Diels-Alder reactions (Tetrahedron Asymmetry 2003, 14, 3313 Serra), and

Cyclization of citral.

Since the end of the 19th century, the acid-catalyzed transformation of citral to unsaturated cyclic alcohols has been known through the work of A. Verley (Bull. Soc. Chim III 1899, 21, 408) as well as O. Zeitschel and H. Schmidt (Journal für praktische Chemie 1932, Volume 133, 370-373), whereby the yields are very low and complex mixtures of substances were obtained. Later on kinetic studies on this transformation from C. Price (Industrial and Engineering Chemistry 1948, 40, 2, 257) and B. Clark (Tetrahedron 1977, 33, 17, 2187) confirmed the cyclization as very complex transformation yielding several cyclic products wherein isopiperitenol appeared to be an intermediate which is not stable under the acidic reaction conditions.

Furthermore, a thermal cyclization starting from citral in the absence of an acid (G. Ohloff, THL 1960, 11, 10) is possible, as well as by adding catalytic quantities of weak

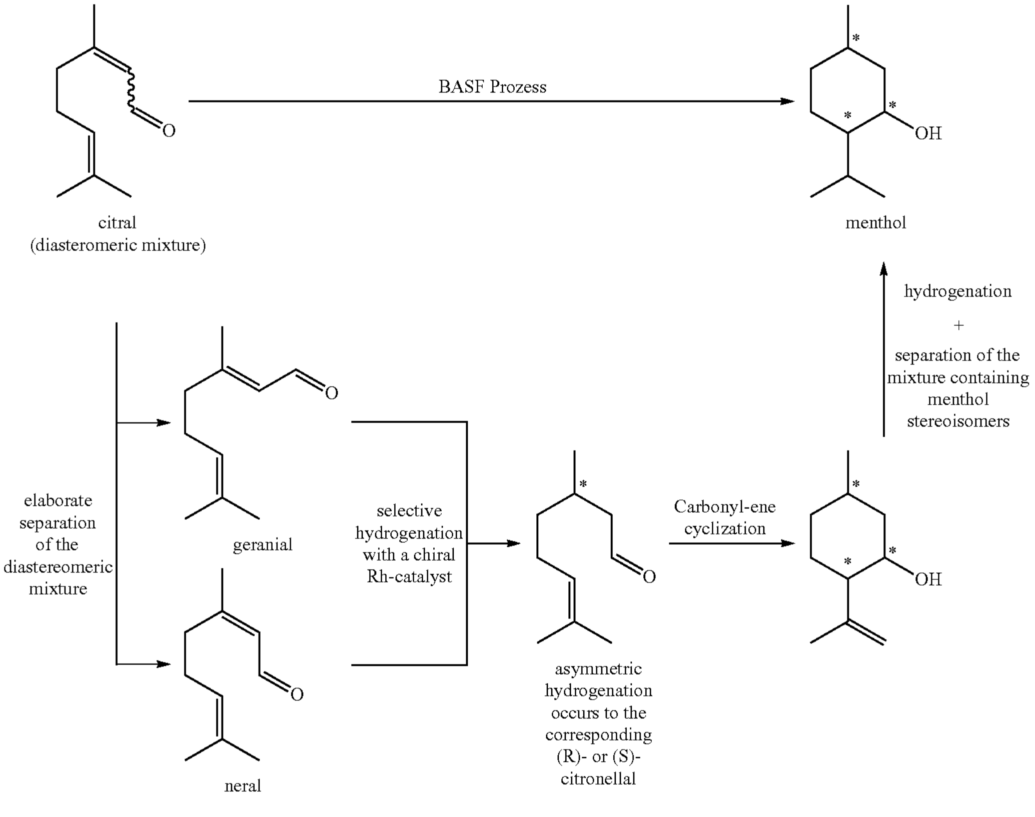

citral
(diasteromeric mixture)
menthol
geranial
neral

Only very few scientific papers and patent applications refer to the synthesis of isopiperitenol as an alternative, industrially useful precursor, and these can be summarized as follows:

C—H oxidations starting from limonene (J.-P. Rioult et al., Flavour Fragr. J. 2000, 15, 223; WO 2004/013339; Verhoeven et al., The Plant Journal 2004, 39, 135), acids (DE2305629C2) leading to the desired product as a mixture of stereoisomers. Although the yields are very good for the latter process since achiral (in)organic acids are applied the product was obtained as a mixture of stereoisomers.

In the prior art, no process for preparing enantiopure isopiperitenol starting from commercially available citral, which can be carried out in a single high yielding steps and in which isopiperitenol is obtained in an enantiopure form, is known.

The problem to be solved by the present invention is to develop a process which allows the production of enantiomerically enriched isopiperitenol as precursor compound of menthol, CBD and of THC, thus overcoming the disadvantages of the prior art.

The inventors have developed a process making use of an asymmetric cyclization to isopiperitenol starting from citral/neral and thus shortening the current industrial process to menthol and opening options to find a variable way to other substances such as Cannabidiol (CBD) and Tetrahydrocannabinol (THC), as exemplified in the following scheme.

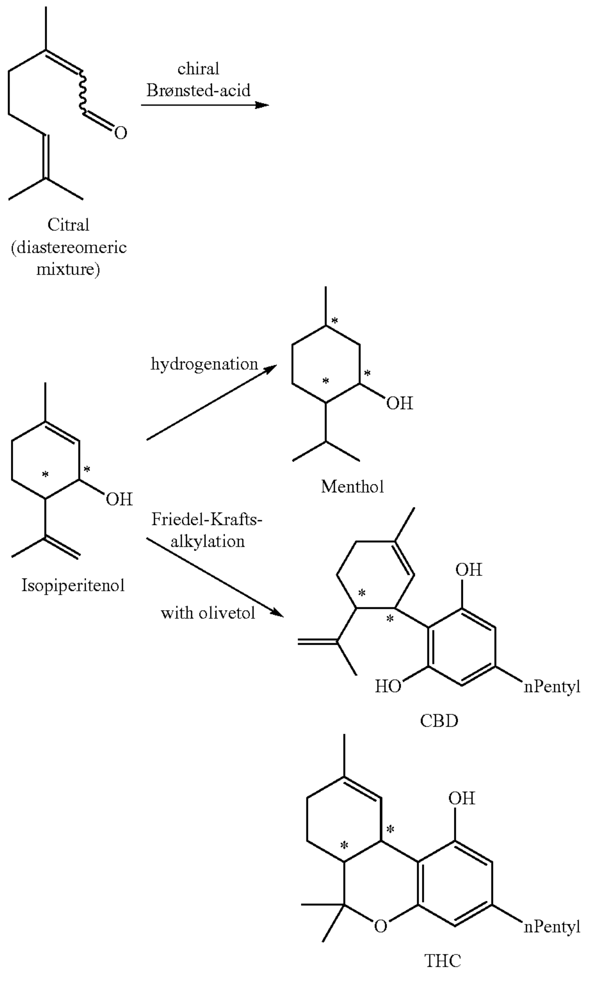

Citral (diastereomeric mixture)
Isopiperitenol
Menthol
CBD
THC

The problem is solved by the provision of an improved process for the asymmetric synthesis of isopiperitenol, wherein Neral [(Z)-3,7-dimethylocta-2,6-dienal] is cyclized, optionally in a solvent, in the presence of a chiral dimeric phosphazene-derived catalyst.

BRIEF DESCRIPTION OF THE DRAWING

The invention will now be described in greater detail with reference to the drawing, wherein:

FIG. 1 shows An exemplary reaction protocol survey for some parameters for different reaction conditions including various substrates and catalysts in differing amounts.

In more detail, the present invention is directed to an improved process for the asymmetric synthesis of isopiperitenol of formula (I), (I)

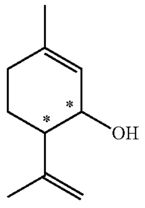

wherein a substrate containing at least one of Neral [(Z)-3,7-dimethylocta-2,6-dienal] and Geranial [(E)-3,7-dimethylocta-2,6-dienal] is subjected to a treatment, optionally in an organic solvent, with a dimeric phosphazene-derived catalyst represented by the following formula (II) whereby a reaction mixture containing isopiperitenol is obtained:

(II)

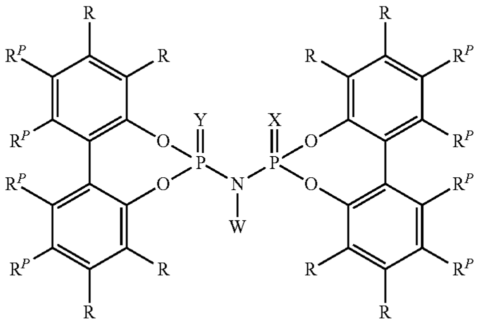

wherein in said formula (II):

R is the same or different on each position and is each selected from hydrogen, halogen, $SF_5$, $NO_2$, cyano, $C_1$ to $C_{20}$ straight chain, branched chain or cyclic aliphatic hydrocarbons, optionally having one or more halogens, preferably F or Cl, $SF_5$, $NO_2$ or cyano on the aliphatic hydrocarbon, $C_6$ to $C_{18}$ aromatic hydrocarbons or $C_5$ to $C_{18}$ heteroaromatic hydrocarbons, each aromatic or heteroaromatic hydrocarbon optionally being substituted by one or more substituents selected from halogen, $SF_5$, $NO_2$, cyano, $C_1$ to $C_{20}$ straight chain, branched chain or cyclic aliphatic hydrocarbons, optionally having one or more halogens, preferably F and/or Cl, $SF_5$, $NO_2$ or cyano on the aliphatic hydrocarbon, $R^P$ is the same or different on each position and has the meaning of R, or two $R^P$ on the same aryl ring may form a ring with each other which may be an aromatic ring structure or an aliphatic ring structure, which aromatic ring structure and/or aliphatic ring structure may be substituted with one or more substituents R, X and Y are the same or different and are either oxygen or $NR^N$, wherein $R^N$ is an electron withdrawing or electron donating group, being the same or different on each position and being selected from:

i. -alkyl, —CO-alkyl, —(CO)—O-alkyl, sulfinyl alkyl, sulfonyl alkyl, sulfonyl iminoalkyl, sulfonyl bisiminoalkyl, phosphinyl dialkyl, phosphonyl alkyl, alkyl phosphorane, N,N'-alkylimidazolidin-2-iminyl wherein alkyl is a $C_1$ to $C_{20}$ straight chain, branched chain or cyclic aliphatic hydrocarbon, optionally having at least one substituent selected from $C_1$ to $C_6$ alkoxy, halogen, preferably F and/or Cl, cyano, nitro, or $SF_5$;

ii. -aryl, —CO-aryl, —(CO)—O-aryl, sulfinyl aryl, sulfonyl aryl, sulfonyl iminoaryl, sulfonyl iminosulfonylaryl, sulfonyl bisiminoaryl, phosphinyl diaryl, phosphinyl alkylaryl, phosphonyl aryl, aryl phosphoranes, aryl alkyl phosphoranes, N,N'-arylimidazolidin-2-iminyl, N-aryl-N'-alkylimidazolidin-2-iminyl wherein aryl is a $C_6$ to $C_{18}$ aromatic hydrocarbon, optionally having at least one substituent selected from $C_1$ to $C_6$ alkyl optionally substituted by at least one halogen, $C_1$ to $C_6$ alkoxy, halogen, preferably F and/or Cl, cyano, nitro, or $SF_5$;

iii. -heteroaryl, —CO-heteroaryl, —(CO)—O-heteroaryl, sulfinyl heteroaryl, sulfonyl heteroaryl, —(P═O)-diheteroaryl, phosphinyl diheteroaryl, phosphinyl arylheteroaryl, phosphinyl heteroaryl alkyl, phosphonyl heteroaryl, heteroaryl phosphoranes, heteroaryl aryl phosphoranes, heteroaryl aryl alkyl phosphoranes, N,N'-heteroarylimidazolidin-2-iminyl, N-heteroaryl-N'-alkylimidazolidin-2-iminyl, N-heteroaryl-N'-arylimidazolidin-2-iminyl wherein heteroaryl is a $C_2$ to $C_{18}$ heteroaromatic hydrocarbon, optionally having at least one substituent selected from $C_1$ to $C_6$ alkyl optionally substituted by at least one halogen, $C_1$ to $C_6$ alkoxy, halogen, preferably F and/or Cl, cyano, nitro, or $SF_5$;

and

W is selected from hydrogen, halogen, a metal selected from Li, Na, K, Rb, Cs, Be, Mg, Ca, Sr, Ba Sc, Ti, V, Cr, Mn, Fe, Co, Ni, Cu, Zn, Y, Zr, Mo, Ru, Rh, Pd, Ag, Cd, W, Re, Os, Ir, Pt, Au, Hg, Al, Ga, In, Ge, Sn, Pb, As, Sb, Bi, Se, Te, La, Sm, Eu, Yb, U or a cationic organic group, a substituted borane —$BR^IR^{II}R^{III}$ or a substituted silicon —$SiR^IR^{II}R^{III}$, wherein $R^I$, $R^{II}$ and $R^{III}$ may be same or different and each stands for hydrogen, halogen, an optionally —O-bonded $C_1$ to $C_{20}$ straight chain, branched chain or cyclic aliphatic hydrocarbon, optionally having one or more unsaturated bonds or one or more hetero atoms in the chain, a $C_5$ to $C_{18}$ heteroaromatic hydrocarbon, a $C_6$ to $C_{18}$ aromatic hydrocarbon or partially arene-hydrogenated forms thereof, each hydrocarbon optionally being substituted by one or more groups selected from $C_1$ to $C_{20}$ straight chain, branched chain or cyclic aliphatic hydrocarbons, or one or more heterosubstituents, W being preferably selected from hydrogen and the substituted silicon —$SiR^IR^{II}R^{III}$, wherein $R^I$, $R^{II}$ and $R^{III}$ are as defined before.

The reaction conditions for the inventive process are not critical and the reaction can be carried out in a temperature range from −100° C. to 30° C. or even higher up to 80° C. The reaction can be carried out neat or in an aprotic organic solvent such as $CH_2Cl_2$, $CHCl_3$, $Et_2O$, THF, PhMe, pentane, hexane, cyclohexane, generally under atmospheric pressure.

In an embodiment of the process, the dimeric phosphazene-derived catalyst has the formula (III):

(III)

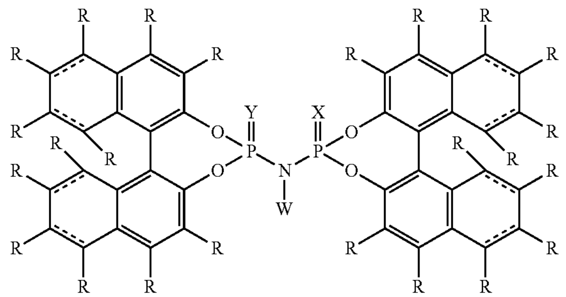

wherein the substituent R is the same or different on each position and is defined as before, X and Y have the meanings as defined before and W represents hydrogen, an alkali metal or an earth alkaline metal.

In an embodiment of the process, the dimeric phosphazene-derived catalyst has the formula (IVa):

(IVa)

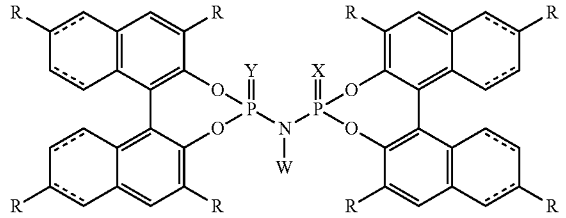

wherein the substituent R is the same or different on each position and is defined as before, X and Y have the meanings as defined before and W represents hydrogen, an alkali metal or an earth alkaline metal.

In the formulae (III), (IVa) and (IVb) below, the broken line represents a double bond, thus demonstrating a naphthalene ring system, or a hydrogenated double bond, demonstrating a 4H-naphthalene ring system, and both forms might be present in the catalysts as used in the inventive process.

In another embodiment of the inventive process, the dimeric phosphazene-derived catalyst is represented by the following formula (IVb):

(IVb)

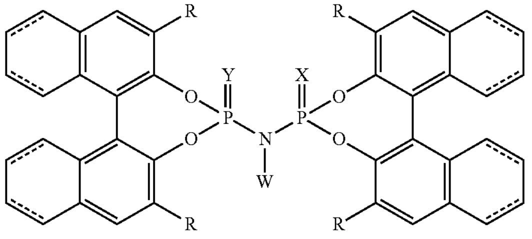

wherein the substituent R is the same or different on each position and is defined as above, X and Y have the meanings as defined above and W represents hydrogen, an alkali metal or an earth alkaline metal.

In another embodiment of the inventive process, in any one of formula (II), (III), (IVa) or (IVb), the substituent R is preferably the same or different on each position and represents halogen, a straight chain, branched chain or cyclic $C_1$ to $C_{20}$ aliphatic hydrocarbon or a $C_6$ to $C_{18}$ aromatic hydrocarbon, said aliphatic hydrocarbon and/or aromatic hydrocarbon being substituted by one or more halogens, preferably F and/or Cl, $SF_5$, $NO_2$ or a straight chain, branched chain or cyclic $C_1$ to $C_{20}$ aliphatic hydrocarbon, being substituted by one or more halogens, preferably F and/or Cl, $SF_5$, $NO_2$ on the aliphatic hydrocarbon, X and Y have the meanings as defined above and W represents hydrogen, an alkali metal or an earth alkaline metal.

In another embodiment of the inventive process, in any one of formula (II), (III), (IVa) or (IVb), Y is defined as O or $NR^N$ and X is defined as $NR^N$, wherein $R^N$ is an electron withdrawing or electron donating group, being the same or different on each position and being selected from:

i. sulfinyl alkyl or sulfonyl alkyl, wherein alkyl is a $C_1$ to $C_{20}$ straight chain, branched chain or cyclic aliphatic hydrocarbon, optionally having at least one substituent selected from $C_1$ to $C_6$ alkoxy, halogen, preferably F and/or Cl, cyano, nitro or $SF_5$;

ii. sulfinyl aryl, or sulfonyl aryl, wherein aryl is a $C_6$ to $C_{18}$ aromatic hydrocarbon, optionally having at least one substituent selected from $C_1$ to $C_6$ alkyl optionally substituted by at least one halogen, $C_1$ to $C_6$ alkoxy, halogen, preferably F and/or Cl, cyano, nitro or $SF_5$;

iii. sulfinyl heteroaryl, or sulfonyl heteroaryl, wherein heteroaryl is a $C_2$ to $C_{18}$ heteroaromatic hydrocarbon, optionally having at least one substituent selected from $C_1$ to $C_6$ alkyl optionally substituted by at least one halogen, $C_1$ to $C_6$ alkoxy, halogen, preferably F and/or Cl, cyano, nitro or $SF_5$; and wherein R has the meaning as defined above, preferably the same or different on each position and represents halogen, a straight chain, branched chain or cyclic $C_1$ to $C_{20}$ aliphatic hydrocarbon or a $C_6$ to $C_{18}$ aromatic hydrocarbon, said aliphatic hydrocarbon and/or aromatic hydrocarbon being substituted by one or more halogens, preferably F and/or Cl, $SF_5$, $NO_2$ or a straight chain, branched chain or cyclic $C_1$ to $C_{20}$ aliphatic hydrocarbon, being substituted by one or more halogens, preferably F and/or Cl, $SF_5$, $NO_2$ on the aliphatic hydrocarbon, and W represents hydrogen, an alkali metal or an earth alkaline metal.

In a preferred embodiment of any of the inventive process, in said formulae (II), (III), (IVa) or (IVb), Y is defined as O or $NR^N$, preferably O, and X is defined as $NR^N$, wherein $R^N$ is an electron withdrawing group and is preferably selected from sulfonyl alkyl, wherein alkyl is a partly or fully halogenated straight chain, branched chain or cyclic $C_1$ to $C_{20}$ aliphatic hydrocarbon, or sulfonyl aryl wherein aryl is a $C_6$ to $C_{18}$ aromatic hydrocarbon, optionally having at least one substituent selected from $C_1$ to $C_6$ alkyl optionally substituted by at least one halogen, $C_1$ to $C_6$ alkoxy, halogen, preferably F and/or Cl, cyano, nitro or $SF_5$, and wherein R has the meaning as defined above, preferably the same or different on each position and represents halogen, a straight chain, branched chain or cyclic $C_1$ to $C_{20}$ aliphatic hydrocarbon or a $C_6$ to $C_{18}$ aromatic hydrocarbon, said aliphatic hydrocarbon and/or aromatic hydrocarbon being substituted by one or more halogens, preferably F and/or Cl, $SF_5$, $NO_2$ or a straight chain, branched chain or cyclic $C_1$ to $C_{20}$ aliphatic hydrocarbon, being substituted by one or more halogens, preferably F and/or Cl, $SF_5$, $NO_2$ on the aliphatic hydrocarbon, and W represents hydrogen, an alkali metal or an earth alkaline metal.

In a further preferred embodiment of the inventive process, the dimeric phosphazene-derived catalyst is represented by the following formula (IVb):

(IVb)

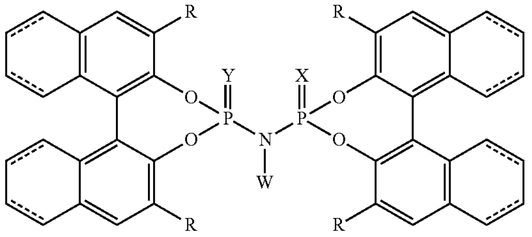

wherein the substituent R is the same or different on each position and is a $C_6$ to $C_{18}$ aromatic hydrocarbon, said aromatic hydrocarbon being substituted by one or more halogens, preferably F and/or Cl, $SF_5$, $NO_2$ or a straight chain, branched chain or cyclic $C_1$ to $C_{20}$ aliphatic hydrocarbon, being substituted by one or more halogens, preferably F and/or Cl, $SF_5$, or $NO_2$ on the aliphatic hydrocarbon, Y is O and X is $NR^N$ wherein $R^N$ is sulfonyl alkyl, wherein alkyl is a partly or fully halogenated straight chain, branched chain or cyclic $C_1$ to $C_{20}$ aliphatic hydrocarbon, the broken line each represents a double bond, and W represents hydrogen, an alkali metal or an earth alkaline metal.

The inventive process allows to use a substrate having a ratio of Neral and Geranial ranging from Neral (Z:E=>99:1) to Geranial (Z:E=<1:99), preferably with a higher content of Neral in the range of more than Z:E=80:20.

It is particularly useful that the obtained reaction mixture comprising isopiperitenol can be additionally subjected to a hydrogenation treatment whereby a reaction mixture containing at least one of menthol, isomenthol, neomenthol and neoisomenthol is obtained. Said hydrogenation treatment of the reaction mixture is generally carried out with hydrogen and a hydrogenation catalyst.

The obtained reaction mixture can be separated into the individual compounds or further reacted with olivetol or substituted derivatives thereof in the presence of a Lewis or Brønsted acid, whereby a reaction mixture containing Cannabidiol (CBD) and/or Tetrahydrocannabinol (THC) and isomers thereof is obtained.

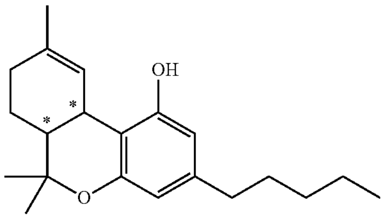

Tetrahydrocannabinol
(THC)

-continued

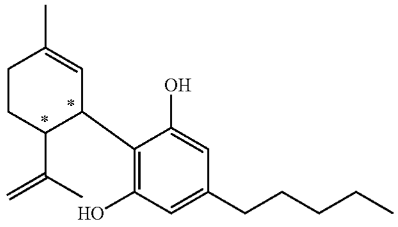

Cannabidiol
(CBD)

Thus, the present invention also allows the preparation of derivatives of THC and CBD to start with a Neral-derivative of the formula (V)

(V)

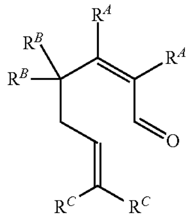

which is cyclized in the presence of a dimeric phosphazene-derived catalyst of the formula (II) as defined above, preferably a catalyst of formula (II), (III), (IVa) or (IVb), as defined in the various modifications above and the reaction mixture is further reacted, in the presence of a Lewis or Brønsted acid, with a substituted olivetol-like, resorcin-based compound of the formula (VI)

(VI)

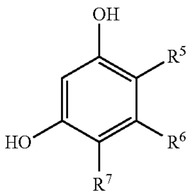

whereby a reaction mixture containing racemic or optically active THC- and/or CBD-analoga of the general formula (VIIa and VIIb) are obtained;

(VIIa)

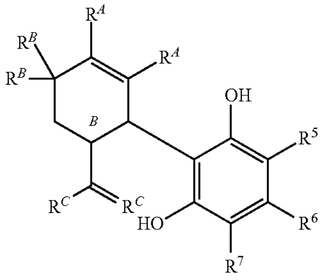

-continued (VIIb)

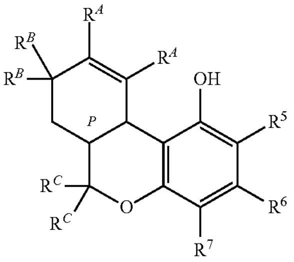

wherein $R^A$ is, independently from each other, the same or different and is each hydrogen, a $C_1$ to $C_6$ alkyl group, in particular methyl, —$CH_2OH$, or —$COOR^e$ with $R^e$ being H or a $C_1$ to $C_6$ alkyl group;

$R^B$ is, independently from each other, the same or different and is each hydrogen, a $C_1$ to $C_6$ alkyl group, in particular methyl; or two of $R^B$ or two of $R^C$, respectively, may form a ring amongst each other, $R^C$ is, independently from each other, the same or different and is each a $C_1$ to $C_6$ alkyl group, in particular methyl; or two of $R^B$ or two of $R^C$, respectively, may form a ring amongst each other, $R^5$ and $R^7$ are, independently from each other, the same or different and are each hydrogen or —$COOR^e$ with $R^e$ being H or a $C_1$ to $C_6$ alkyl group;

$R^6$ represents hydroxy, a $C_1$ to $C_{12}$, preferably $C_3$ to $C_7$, alkyl group, optionally being further substituted by one or more hydroxyl groups.

Particularly for a continuous process, it is desirable to use a catalyst of any of formulae (II), (III), (IVa) or (IVb) in an immobilized form in any of the processes as described above.

In one embodiment, the dimeric phosphazene-derived catalysts of formula (II), wherein Y, X and R are as defined above, can be bound to a solid support, optionally through a linker, wherein the linker is an aliphatic, heteroaliphatic, aromatic or heteroaromatic hydrocarbon group, each hydrocarbon group having up to 50 carbon atoms and each optionally being further substituted by one or more heterosubstituents, aliphatic, heteroaliphatic, aromatic or heteroaromatic hydrocarbon groups, each hydrocarbon group optionally being substituted by one or more heterosubstituents; and wherein the solid support is insoluble in the reaction mixture and is selected from wool, cotton, polystyrene, polysiloxane, polyacrylate, polyethylene, polypropylene, polyethylene glycol and polyamide, and copolymers thereof, each optionally having at least one halogen, preferably F and/or Cl, hydroxy, sulfonyl, alkoxy, halogen-substituted alkoxy on the aliphatic hydrocarbon and/or oxygen in the aliphatic hydrocarbon chain.

In another embodiment, the dimeric phosphazene-derived catalysts catalyst of formula (II), (III), (IVa) or (IVb) as defined above can be bound to a solid support via a linker between the solid support and the aromatic or cycloaliphatic backbone, preferably in the 6-position of one, two, three or all aromatic or cycloaliphatic backbones of the dimeric phosphazene-derived catalyst, wherein the linker and the solid support are as defined above.

In yet another embodiment, the dimeric phosphazene-derived catalysts of the formula (II), (III), (IVa) or (IVb) as defined above may be bound to a solid support as a stationary phase via linker between the $NR^N$ substituent and the solid support wherein in the dimeric phosphazene-derived catalyst of the formula (II), (III), (IVa) or (IVb), Y is O or $NR^N$, X is $NR^N$, wherein $R^N$ is a straight or branched alkyl chain or a polyether alkyl chain, said alkyl chain having at least one halogen, preferably fluorine, and wherein R and $R^P$ are as defined abovesuch as a sulfonated tetrafluoro ethylene polymer Nafion® as solid support.

Description of the Process:

Currently, Neral and Geranial may be synthezised by allylic oxidation of Nerol and Geraniol using $MnO_2$ yielding the corresponding aldehydes in Z:E purity of at least 96:4 (in case of Neral) and 2:98 (or more for Geraniol in case of Geranial) after subsequent destillation.

The catalyst used here is based on imidodiphosphate (IDP) catalyst, the iminoimidodiphosphorimidate (iIDP) catalyst (List et al., J. Am. Chem. Soc. 2016, 138, 34, 10822) and imidodiphosphorimidate (IDPi) catalyst and may be prepared using the process as described in EP20200632.6. Used solvents are dried before use.

The catalyst can be dissolved in a solvent and cooled to different temperatures depending on the solvent used. The Neral was added and the reaction was stirred and stopped, for example upon addition of triethylamine after a certain time.

Definitions

The following definitions apply to the individual groups R, $R^P$, $R^N$ and W equally as follows.

A heterosubstituent as defined according to the invention can be selected from OH, F, Cl, Br, I, CN, $NO_2$, I—$R^s{}_2$, NO, NCO, —NCS, —SCN, $SO_3H$, a monohalogenomethyl group, a dihalogenomethyl group, a trihalogenomethyl group, $CF(CF_3)_2$, $SF_5$, aliphatic, aromatic, heteroarmatic, primary, secondary, tertiary amine or ammonium bound through N atom, —O-alkyl (alkoxy), —O-aryl, —O-heteroaryl —O—$SiR^s{}_3$, —S—S—$R^s$, —S—$R^s$, —S(O)—$R^s$, —$S(O)_2$—$R^s$, —COOH, —$CO_2$—$R^s$, —$BR^s{}_2$, —$PR^s{}_2$, —$OPR^s{}_2$, amide, bound through C or N atom, formyl group, —C(O)—$R^s$, —COOM, where M is a metal such as Li, Na, K, Cs, Ag. $R^s$ may be, independently from each other, the same or different and is each an aliphatic, heteroaliphatic, aromatic or heteroaromatic group, each optionally being further substituted by one or more heterosubstituents, aliphatic, heteroaliphatic, aromatic or heteroaromatic groups; and/or optionally bridged by an —O-atom, represents a halogenide Aliphatic hydrocarbons including alkyl, alkenyl and alkinyl and may comprise straight-chain, branched and cyclic hydrocarbons.

Heteroaliphatic is a hydrocarbon including alkyl, alkenyl and alkinyl which may comprise straight-chain, branched and cyclic hydrocarbons with one or more carbon atoms substituted with at least one heteroatom.

In more detail, $C_1$-$C_{20}$-alkyl can be straight chain or branched and has 1, 2, 3, 4, 5, 6, 7, 8, 9, 10, 11, 12, 13, 14, 15, 16, 17, 18, 19 or 20 carbon atoms. Alkyl might be $C_1$-$C_6$-alkyl, in particular methyl, ethyl, propyl, isopropyl, butyl, isobutyl, sec-butyl or tert-butyl, likewise pentyl, 1-, 2- or 3-methylpropyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl. Substituted alkyl groups are trifluoromethyl, pentafluoroethyl and 1,1,1-trifluoroethyl.

Cycloalkyl might be cyclopropyl, cyclobutyl, cyclopentyl, cyclohexyl or cycloheptyl. Alkenyl might be $C_2$-$C_{20}$ alkenyl. Alkinyl might be $C_2$-$C_{20}$ alkinyl.

Said unsaturated alkenyl- or alkinyl groups can be used for linking the inventive compounds to a carrier such as a polymer to serve for an immobilized catalyst.

Halogen is F, Cl, Br or I.

Alkoxy is preferably $C_1$-$C_{10}$ alkoxy such as methoxy, ethoxy, propoxy, tert-butoxy, butoxy, pentoxy, hexyloxy, etc and isomers thereof.

$C_3$-$C_8$-Heterocycloalkyl having one or more heteroatoms selected from among N, O and S is preferably 2,3-dihydro-2-, -3-, -4- or -5-furyl, 2,5-dihydro-2-, -3-, -4- or -5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl.

Optionally substituted means unsubstituted or monosubstituted, disubstituted, trisubstituted, tetrasubstituted, pentasubstituted, or even further substituted for each hydrogen, such as persubstituted, on the hydrocarbon.

Aryl might be a $C_6$ to $C_{22}$ aromatic hydrocarbon and may be phenyl, naphthyl, anthracenyl, phenanthryl or biphenyl Arylalkyl might be benzyl.

Heteroaryl may be a $C_5$ to $C_{18}$ heteroaromatic hydrocarbon and may have one or more heteroatoms selected from among N, O and S, and is preferably 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, also preferably 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-Indolyl, 4- or 5-isoindolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, also preferably 1,3-benzodioxol-5-yl, 1,4-benzodioxan-6-yl, 2,1,3-benzothiadiazol-4- or -5-yl or 2,1,3-benzoxadiazol-5-yl.

Experimental Part

Materials and Characterization

Chemicals: Chemicals (Abcr, Acros, Aldrich, Gelest, Fluka, Fluorochem, Strem, TCI) were purchased as reagent grade and used without further purification unless indicated otherwise. Neral and Geranial may be synthezised by allylic oxidation of Nerol and Geraniol using $MnO_2$ yielding the corresponding aldehydes in Z:E purity of at least 96:4 (in case of Neral) and 2:98 (in case of Geranial) after subsequent destillation.

Solvents: Solvents ($CH_2Cl_2$, $CHCl_3$, $Et_2O$, THF, PhMe) were dried by distillation from an appropriate drying agent in the technical department of the Max-Planck-Institut für Kohlenforschung and received in Schlenk flasks under argon. The other solvents (n-pentane and pyridine) were purchased from commercial suppliers and dried over molecular sieves.

Glassware: Screw-cap vials, round-bottom flasks or Schlenk-flasks were used for the reactions unless indicated otherwise. Thin Layer Chromatography: Thin-layer chromatography (TLC) was performed using silica gel pre-coated plastic sheets (Polygram SIL G/UV254, 0.2 mm, with fluorescent indicator; Macherey-Nagel), which were visualized with a UV lamp (254 or 366 nm) and stained with potassium permanganate ($KMnO_4$). $KMnO_4$-stain: $KMnO_4$ (1.5 g), $K_2CO_3$ (10 g), 10% NaOH (1.25 mL) in water (200 mL).

Flash Column Chromatography: Flash column chromatography (FCC) was carried out using Merck silica gel (60 Å, 230-400 mesh, particle size 0.040-0.063 mm) using technical grade solvents. Elution was accelerated using compressed nitrogen. All reported yields, unless otherwise specified, refer to spectroscopically and chromatographically pure compounds.

Gas Chromatography: Gas chromatography (GC) analyses on a chiral solid support were performed on HP 6890 and 5890 series instruments (split-mode capillary injection system, flame ionization detector (FID), hydrogen carrier gas). All the analyses were conducted in the GC department of the Max-Planck-Institut für Kohlenforschung. The conditions employed are described in detail in the individual experiments.

Catalyst Synthesis

The catalysts used in the present invention were synthesized by means of the process using the phosphazene reagent as disclosed in EP application 20200632.6 or the preparation according to WO 2017/037141.

Procedure for the Catalyst Synthesis:

A flame-dried Schlenk was charged with phosphazene reagent and the corresponding substituted (S)- or (R)-BINOL or Biphenol (2.0 equiv.). Dry pyridine was added and both solids dissolve to give a clear solution. The amount of pyridine is 1 mL for approximately 50 mg of used phosphazene reagent. The clear solution slowly forms a precipitate and after 3 h the sulfonamide (5.0 equiv.) is added to the reaction which then stirred overnight. Water (10 wt %) was added to the reaction and stirred for further 3 hours. The reaction was worked up after addition of excess of aq. HCl (10%) and the aqueous phase was extracted with $CH_2Cl_2$. The combined organic layers were washed with brine, dried over $NaSO_4$ and the solvent was evaporated. The catalyst was purified by column chromatography and acidified with DOWEX.

Acidification with DOWEX:

A column was charged with DOWEX, which was washed with 0.05 M aq. $H_2SO_4$ and $CH_2Cl_2$. The purified catalyst was dissolved in $CH_2Cl_2$ and then passed through the column, which was rinsed with $CH_2Cl_2$ until no UV active material is released. The solvent was evaporated and the catalyst was obtained. After drying in high vacuum and the corresponding catalyst was analyzed by NMR and MS.

Exemplary Reaction Protocol for the Inventive Process

An exemplary catalytic asymmetric cyclization of Citral, Neral, Geranial is given as follows.

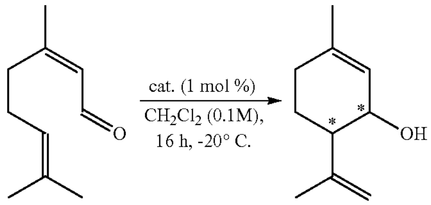

-continued

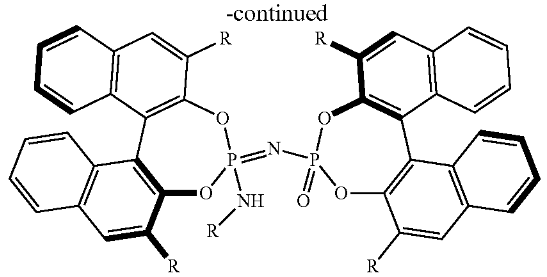

A screw-cap vial was charged with a magnetic stirrer bar, iIDP-catalyst (1 mol %) and dichloromethane (0.1 M). The reaction solution was cooled to −20° C. and stirred for 10 min. Neral (ratio of Z:E 96:4) was added to the reaction vial and the reaction stirred for 16 h at aforementioned temperature. The reaction mixture was treated with $Et_3N$ and then the reaction was slowly warmed to room temperature. The solvent was evaporated at 40° C. and 500 mbar. The reported yields are determined by NMR using mesitylene or triphenylmethane as internal standards.

An exemplary reaction protocol survey for some parameters is shown in FIG. 1 for different reaction conditions including various substrates and catalysts in differing amounts. According to the results, it is shown that the general reaction protocol is applicable in various conditions and to various substrates.

Experimental Results

Catalyst Classes

Several Brønsted acid catalysts (organic or inorganic and achiral or chiral acids) covering a broad range on the pKa-scale are able to catalyze the cyclization reaction of citral. Weak acids (pKa>10 in MeCN) show little conversion but maintain a clean reaction profile whereas strong acids (pKa<8 in MeCN) result in a more complex reaction profile. The complexity of the reaction using stronger acids could be explained by a fast decomposition pathway of the cyclized intermediate, isopiperitenol, to several elimination products (e.g. trienes) as stated in the literature. Catalyst classes (IDP, iIDP and IDPi) ranging on the pKa-scale between weak and strong acids are able to combine both advantages, higher conversion to the desired product and maintain a clean reaction profile.

Concentration

The cyclization reaction of citral can be performed in several organic solvent with different concentrations ranging from neat to very dilute 0.005 M reaction conditions. The diastereomeric and enantiomeric excess of the desired cyclized product are nearly constant under different dilutions of the reaction mixture. Control experiments were executed by determination of the enantiomeric excess at different stages of the reaction to exclude a kinetic resolution in the decomposition pathway of the product.

Catalyst Loading

The cyclization reaction of Citral can be performed by using different catalyst loadings ranging from 0.05 to 100 mol % depending on the used solvent and temperature without significant loss of diastereomeric and enantiomeric excess of the desired product.

Water Content/Molesieves

The cyclization reaction of citral can be performed under modified reaction conditions (e.g. in the presence of water) wherein similar diastereomeric and enantiomeric ratios are obtained.

Conclusion

The cyclization reaction of citral/neral using an inventive catalyst can be performed ranging from temperatures of −80° C. to 25° C., reaction times from 30 minutes to 48 h, concentrations from neat to 0.005 M in several solvents and catalyst loadings from 0.05 mol % to 100 mol %. The screening of various catalysts is shown in FIG. 1. The cyclization reaction of Citral is performed in high yields when catalysts bearing electron-deficient groups are used. Screening of several different cores in combination with the best 3,3'-substituent lead to the conclusion that the smallest inner core $CF_3$ furnishes the product in the highest yield and diastereomeric as well as enantiomeric ratios under optimized standard reaction conditions.

An exemplary catalytic asymmetric cyclization of Citral, Neral, Geranial is shown above.

Isolation of the Product and Catalyst Recovery

A round-bottom flask was charged with a magnetic stirrer bar, iIDP-catalyst (2.5 mol %) and dry pentane (0.1 M) and was cooled to the 0° C. After 20 minutes, Neral (5.8 mmol, ratio 96:4) was added to the reaction flask and the reaction stirred for 16 h at aforementioned temperature. The reaction mixture was treated with triethylamine and then the reaction was slowly warmed to room temperature. Upon evaporation of the solvent, a reaction crude containing the cyclized product was obtained. Purification of the crude reaction mixture by CC (silica) afforded the cyclic, allylic alcohol (40% yield, d.r. 12:1 (trans:cis), e.r. 96:4)

Synthesis of Different Substrates and Cyclisation Thereof (Z)-4,4,7-trimethylocta-2,6-dienal 4,4,7-trimethyloct-6-en-2-ynal

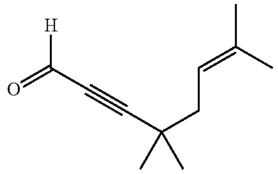

To a stirred solution of $CBr_4$ (16.55 g, 49.9 mmol, 2.0 equiv.) in $CH_2Cl_2$ (20 mL) was added triphenylphosphine (26.2 g, 99.8 mmol, 4.0 equiv.) at 0° C., and the resulting reaction mixture stirred for 15 minutes. To this suspension was added (Z)-4,4,7-trimethylocta-2,6-dienal (prepared according to Schindler et al., *Science* 2018, 361, 1363-1369) (3.5 g, 24.9 mmol, 1.0 equiv.) in $CH_2Cl_2$ (15 mL), and the mixture was stirred for 30 min at room temperature. The reaction mixture was quenched with $H_2O$, and the aqueous layer was extracted with $CH_2Cl_2$. The combined organic layer was washed with $H_2O_2$ (5% in $H_2O$), water, brine, dried over $Na_2SO_4$, and evaporated. The crude reaction product was then dissolved in THF (130 mL) and nBuLi (2.5 M in hexane, 24 mL, 59.9 mmol, 2.4 equiv.) was added dropwise at −78° C. The reaction mixture was slowly warmed to 0° C. and stirred for 20 minutes before the reaction was left to reach room temperature. After full conversion of the starting material the reaction was quenched with saturated aqueous $NH_4Cl$ solution, and the aqueous layer was extracted with diethyl ether. The combined organic layer was washed with brine, dried over $Na_2SO_4$, and the solvent was evaporated under reduced pressure The resulting crude mixture was purified by flash column chromatography (10% DCM/pentane) to obtain 4,4,7-trimethyloct-6-en-2-ynal as a colorless oil (1.74 g, 42% yield).

(Z)-4,4,7-trimethylocta-2,6-dienal

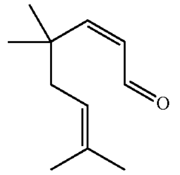

A flame-dried flask was charged with 4,4,7-trimethyloct-6-en-2-ynal (500 mg, 3.0 mmol, 1.0 equiv.), a solvent mixture of cyclohexane/ethylacetate (1:5) and quinoline (0.36 mL, 3.0 mmol, 1.0 equiv.). The Lindlar-catalyst was added at room temperature and the reaction suspension was subjected to hydrogenation conditions (1 atm $H_2$ via balloon). After nearly full conversion the reaction was filtered over Celite pad which was washed extensively with EtOAc. The solvent was evaporated under reduced pressure and the crude product was purified by flash column chromatography to obtain the desired α,β-unsaturated aldehyde 4,4,7-trimethylocta-2,6-dienal as a pale-yellow oil (120 mg, 24% yield) and a mixture of diastereoisomers (Z:E=93:7).

Cyclization of (Z)-4,4,7-trimethylocta-2,6-dienal

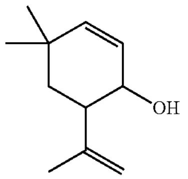

The cyclization reaction was performed according to the general reaction procedure and yielded the desired cyclic allylic alcohol in 95% yield (d.r.=98:2, e.r. (major)=0.4:99.6).

(Z)-2,7-dimethylocta-2,6-dienal ethyl (Z)-2,7-dimethylocta-2,6-dienoate

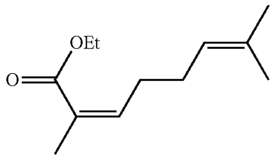

To a stirred solution of ethyl 2-(bis(2,2,2-trifluoroethoxy)phosphoryl)propanoate (925 mg, 2.67 mmol, 1.0 equiv.) in THF (21 mL) was added 18-crown-6 (735 mg, 2.78 mmol, 1.05 equiv.) in THF. The reaction was cooled to −78° C. and KHMDS (5.3 mL, 2.67 mmol, 0.5 M solution in PhMe) was added dropwise to the reaction. After stirring at −78° C. for 20 minutes, 5-methylhex-4-enal (prepared following the literature Braddock et al., *Chem. Commun.* 2006, 2483 and Nakada et al., *Tett. Let.* 2014, 55, 50, 6847) (300 mg, 2.67 mmol, 1.0 equiv.) was added and stirred until full conversion at the same temperature. After full conversion the reaction was quenched with sat. aq $NH_4Cl$. The organic phase was separated, and the aqueous phase was extracted with diethyl ether. The combined layers were washed with water and brine, dried over $Na_2SO_4$, filtered and the filtrate was concentrated under reduced pressure. The resulting residue was purified by flash column chromatography to obtain the α,β-unsaturated ester (223 mg, 42% yield).

(Z)-2,7-dimethylocta-2,6-dienal

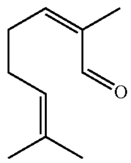

A flame-dried flask was charged with ethyl (Z)-2,7-dimethylocta-2,6-dienoate (344 mg, 1.75 mmol, 1.0 equiv.) and DCM (7 mL) and DIBAL-H was added dropwise (3.8 mL, 1 M in, 3.8 mmol, 2.2 equiv.) at −78° C. After full conversion of the starting material to the desired alcohol the reaction was quenched with a 1:1 mixture water/MeOH. The mixture stirred for 2 h at room temperature. The resulting gel was filtered over a $Na_2SO_4$/Celite pad, which was extensively washed with dichloromethane. The solvent was evaporated under reduced pressure and the crude reaction product (Z)-2,7-dimethylocta-2,6-dien-1-ol was again dissolved in DCM (2 mL). Manganese dioxide (685 mg, 7.89 mmol, 4.5 equiv.) was added to the reaction flask and the reaction stirred at room temperature until full conversion of the starting material. After full conversion the reaction was filtered over a pad of Celite, which was extensively washed with DCM. The solvent was evaporated under reduced pressure and the resulting crude product purified by flash column chromatography to yield (Z)-2,7-dimethylocta-2,6-dienal as a mixture of diastereoisomers (160 mg, 60% yield, Z:E=86:14).

Cyclization of (Z)-2,7-dimethylocta-2,6-dienal

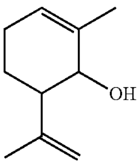

The cyclization reaction was performed according to the general reaction procedure and yielded the desired cyclic allylic alcohol in 72% yield (d.r.=2:1, e.r. (major)=97:3, e.r. (minor)=93:7).

Synthesis of CBD and THC

A reaction vessel was charged with a chiral catalyst phosphoric acid, IDP-, iIDP- or IDPi-catalyst (5 mol %) and anhydrous $CH_2Cl_2$ (0.1M), olivetol (1.1 equiv.) and enantiomerically pure isopiperitenol (0.3 mmol) were added via syringe. The reaction was stirred at room temperature and was quenched with triethylamine upon full conversion of isopiperitenol. The solvents were evaporated and a reaction mixture containing CBD and/or THC compounds ($\Delta^9$-THC (cis and trans), $\Delta^8$-THC, $\Delta^9$-regio-THC (cis and trans) was obtained.

Synthesis of a Reaction Mixture Containing Cannabidiol (CBD)

To a screw-cap vial was added 5-20 mol % catalyst or a Lewis acid (e.g. $BF_3OEt_2$), dry $CH_2Cl_2$, olivetol and the purified enantiomerically pure isopiperitenol. The reaction mixture intensified its color, which faded after few minutes. The reaction mixture was stirred at room temperature and was treated with triethylamine upon full conversion of the two starting materials. The solvents were evaporated and purification of the crude reaction mixture by CC (silica) afforded cannabidiol as the major compound.

Synthesis of a Reaction Mixture Containing Cannabidiol (CBD)

To a flamed-dried Schlenk tube, olivetol (1 mmol, 180 mg), isopiperitenol (cis:trans=5:1, 1.5 eq, 0.16 mL), and $BF_3 \cdot Et_2O$ (62.5 μL, 0.5 mmol) in 6.25 mL DCM were added accordingly at 0° C. under argon. After 1.5 h, the starting material was full consumed as indicated by TLC (5-20% EtOAc/hexane). The reaction was quenched by 100 mg $NaHCO_3$, filtered and washed with DCM. The solvent was evaporated under reduced pressure and the crude mixture was purified by flash column chromatography ($SiO_2$, 5-30% EtOAc/hexane). Three major compounds could be isolated whereas on of them is CBD (32% yield, 101.2 mg).

Synthesis of a Reaction Mixture Containing THC

A flame-dried Schlenk flask was charged with molesieves and 5 mol % iIDP-catalyst. Dry $CH_2Cl_2$, olivetol and the purified enantiomerically pure isopiperitenol were added to the flask. The reaction mixture intensified its color, which faded after few minutes. The reaction was stirred at room temperature and was quenched with $Et_3N$ upon full conversion of the two starting materials. The solvents were evaporated and purification of the crude reaction mixture by preparative TLC afforded THC substances ($\Delta^9$-THC (cis and trans), $\Delta^8$-THC, $\Delta^9$-regio-THC (cis and trans) as the major product.

One-Pot Synthesis of CBD/THC

A reaction vessel was charged with iIDP catalyst (5 mol %) and anhydrous $CH_2Cl_2$ (0.1 M). After cooling the reaction to the desired temperature and stirring for few minutes, Neral (0.3 mmol) was added to the reaction mixture and the reaction stirred for a certain amount of time. After reaching full conversion of the starting materical, olivetol (1 equiv.) was added to the reaction mixture and the reaction was allowed to reach room temperature. Upon full conversion of olivetol, the reaction was quenched with triethylamine. The solvents were evaporated and a reaction mixture containing CBD and/or THC substances ($\Delta^9$-THC (cis and trans), $\Delta^8$-THC, $\Delta^9$-regio-THC (cis and trans) was obtained.

$\Delta^8$-THC Synthesis:

To a flame-dried Schlenk flask, olivetol (36 mg, 0.2 mmol), enantiopure isopiperitenol (d.r. cis:trans=5:1, 1.1 eq.) and $BF_3 \cdot Et_2O$ (0.2 equiv.) in 4 mL DCM were added accordingly at 60° C. under argon. After 14 h, the starting material (olivetol) was fully converted indicated by TLC analysis (with 5% EtOAc/hexane) and the reaction was treated with one drop of triethylamine. The solvent was evaporated under reduced pressure and the crude mixture was purified by flash column chromatography ($SiO_2$, 5% EtOAc/hexane) to afford $\Delta^8$-THC as the desired product (53% yield, 33.3 mg, e.r. 99:1)

$\Delta^9$-THC Synthesis:

To a flame-dried Schlenk flask, olivetol (0.42 mmol, 75.7 mg), isopiperitenol (cis:trans=5:1, 73 μL, 1.1 eq.), and $BF_3 \cdot Et_2O$ (0.2 equiv.) in 8 mL DCM were added accordingly at r.t. under Ar. After 22 h, the ratio of formed products are THC:CBD=2.3:1 and after 42 h, THC:CBD=13.5:1. The reaction was quenched by one drop of triethylamine. The solvent was evaporated under reduced pressure and the crude reaction mixture was purified by flash column chromatography ($SiO_2$, 5% EtOAc/hexane) to afford $\Delta^9$-THC as the desired product (55% yield, 72 mg)

Exemplary Hydrogenation of Isopiperitenol:

The heterogeneous hydrogenation catalyst (64 mg, 10 mol % Pt/C, 0.2 equiv.) was transferred into a round bottom flask and a solution of corresponding isopiperitenol in methanol (3 mL, 0.2M) was added to the reaction flask. The reaction mixture was flushed with hydrogen (1 atm) and the reaction stirred vigorously for 48 h at room temperature under hydrogen atmosphere (1 atm). Upon full conversion of the starting material, the heterogeneous catalyst was removed via filtration and the filtrate was evaporated to yield a reaction mixture containing menthol, isomenthol, neomenthol and neoisomenthol.

Menthol:

A flame-dried flask was charged with enantioenriched isopiperitenol (d.r.=11:1, e.r. 98.5:1.5) (31 mg, 0.20 mmol, 1.0 eq), 3 mL MeOH and Lindlar-catalyst (48.7 mg, 0.11 eq.). After stirring for few minutes, the reaction was submitted to 1 atm of $H_2$-gas (via balloon). After 2 d the reaction reached full conversion (indicated by TLC) and was filtered. After evaporation of the solvent the crude reaction mixture was submitted to GC analysis (>99% conversion, 92% product, ratio of menthol to isomenthol 74.3:25.7, e.r. (menthol/isomenthol)=98.5:1.5).

Synthesis of Solid Supported Catalysts 2-(allyloxy)-1,1,2,2-tetrafluoroethane-1-sulfonamide A flame-dried schlenk flask was equipped with a magnetic stir bar and ammonia (~25 mL, excess) was condensed into the reaction flask at −78° C. 5.0 g of 1,1,2,2-tetrafluoro-2-(3-hydroxypropoxy)ethane-1-sulfonyl fluoride (1.0 eq., 21 mmol) were slowly added to the flask and the reaction stirred for 1.5 h at the aforementioned temperature before gradually warming up to room temperature. After further 1.5 h, the resulting white slurry was acidified with 1M $H_2SO_4$ to a pH of about 2. The aqueous layer was extracted with diethyl ether and the obtained organic layer was dried with $Na_2SO_4$, concentrated under reduced pressure. The corresponding sulfonamide was obtained as colorless solid after drying under high vacuum (4.9 g, 90% yield).

The catalysts used in the following preparation of solid supported confined acids were prepared by using 2-(allyloxy)-1,1,2,2-tetrafluoroethane-1-sulfonamide and following the general reaction protocol.

Synthesis of Solid Styrene-Divinylbenzene Supported: Catalyst

In a flame-dried reaction tube, the corresponding iIDP (50 mg, 0.026 mmol) was dissolved in 0.25 mL chloroform. Styrene (0.5 mL, 4.35 mmol), divinylbenzene (0.25 mL, 1.76 mmol) (prior to use filtered through a short pad of silica) and AIBN were added to the flask. The resulting mixture was placed in a tube and the copolymerization was carried out at 80° C. After 16 h the heating source was removed and the obtained solid was crashed. The resulting polymeric powder was extensively washed with dichloromethane and was acidified by suspending in 6M HCl for 3 h. The suspension was filtered and washed with water and dichloromethane. The obtained solid-supported catalyst was dried in high vacuum overnight at 40° C.

Synthesis of Solid-Supported Sulfonamide:

Nafion® R-1100 resin (sulfonyl fluoride form, 500 mg) was grounded into a fine greyish powder using a cryomill at −196° C. The obtained powder was suspended in anhydrous DMF (3 mL) and an excess of liquid ammonia was condensed in the reaction flask at −78° C. The interface reaction was carried out with continuous stirring. After stirring overnight in liquid ammonia at an initial temperature of −78° C., the residual ammonia was released and the mixture was heated from room temperature to 90° C. for 2 h. The resulting solid-supported sulfonamide was precipitated from water, washed with deionized water and dried under vacuum at 60° C. for 24 h. (497 mg, quant. The corresponding solid-supported catalyst was prepared using the general procedure as stated before.

Exemplary Catalytic Asymmetric Cyclization of Citral, Neral, Geranial Using a Solid-Supported Catalyst:

A screw-cap vial was charged with a magnetic stirrer bar, solid-supported iIDP-catalyst and dry n-pentane (0.5 M). Neral (Z:E 96:4) was added to the reaction vial and the reaction stirred overnight at room temperature. After full conversion of the starting material the solid-supported catalyst was removed using a syringe filter, the filter further rinsed with pentane and the obtained filtrate was treated with trimethylamine. Upon evaporation of the solvent, the yields and d.r. were determined by NMR spectroscopy using mesitylene as an internal standard and the enantiomeric excess was determined by GC. (28% yield, d.r. 15:1 (trans:cis), e.r. 96:4)

Cyclization of Neral Using the Solid-Supported Catalysts

A flame-dried vial was charged with 10 mol % solid-supported catalyst and dichloromethane. Neral (5 μL) was added to the vial and the reaction stirred at room temperature for 16 h. After quenching the reaction with a drop of triethylamine the reaction was filtered and reaction was analyzed by 1H-NMR spectroscopy using an internal standard. The desired product was obtained in 13% yield (d.r. (trans/cis)=5:1, e.r.=96:4). The enantiomeric and diastereomeric ratio was determined by GC analysis.

The invention claimed is:

1. A process for the asymmetric synthesis of isopiperitenol of formula (I), (I)

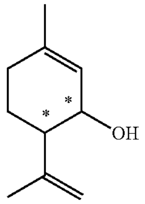

comprising subjecting a substrate containing at least one of Neral [(Z)-3,7-dimethylocta-2,6-dienal] and Geranial [(E)-3,7-dimethylocta-2,6-dienal] to a treatment, optionally in an organic solvent, with a dimeric phosphazene-derived catalyst represented by the following formula (II) whereby a reaction mixture containing isopiperitenol is obtained:

(II)

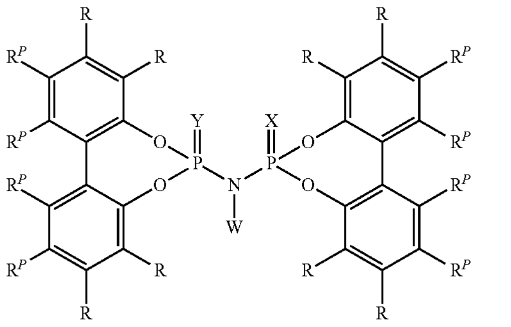

wherein in said formula (II):

R is the same or different on each position and is each selected from hydrogen, halogen, $SF_5$, $NO_2$, cyano, $C_1$ to $C_{20}$ straight chain, branched chain or cyclic aliphatic hydrocarbons, optionally having one or more halogens, $SF_5$, $NO_2$ or cyano on the aliphatic hydrocarbon, $C_6$ to $C_{18}$ aromatic hydrocarbons or $C_5$ to $C_{18}$ heteroaromatic hydrocarbons, each aromatic or heteroaromatic hydrocarbon optionally being substituted by one or more substituents selected from halogen, $SF_5$, $NO_2$, cyano, $C_1$ to $C_{20}$ straight chain, branched chain or cyclic aliphatic hydrocarbons, optionally having one or more halogens, $SF_5$, $NO_2$ or cyano on the aliphatic hydrocarbon, $R^P$ is the same or different on each position and has the meaning of R, or two $R^P$ on the same aryl ring may form a ring with each other which may be an aromatic ring structure or an aliphatic ring structure, which aromatic ring and/or aliphatic ring structure may be substituted with one or more substituents R, X and Y are the same or different and are either oxygen or $NR^N$; wherein:

$R^N$ is an electron withdrawing or electron donating group, being the same or different on each position and being selected from:

i. -alkyl, —CO-alkyl, —(CO)—O-alkyl, sulfinyl alkyl, sulfonyl alkyl, sulfonyl iminoalkyl, sulfonyl bisiminoalkyl, phosphinyl dialkyl, phosphonyl alkyl, alkyl phosphorane, N,N'-alkylimidazolidin-2-iminyl wherein alkyl is a $C_1$ to $C_{20}$ straight chain, branched chain or cyclic aliphatic hydrocarbon, optionally having at least one substituent selected from $C_1$ to $C_6$ alkoxy, halogen, cyano, nitro, or $SF_5$;

ii. -aryl, —CO-aryl, —(CO)—O-aryl, sulfinyl aryl, sulfonyl aryl, sulfonyl iminoaryl, sulfonyl iminosulfonylaryl, sulfonyl bisiminoaryl, phosphinyl diaryl, phosphinyl alkylaryl, phosphonyl aryl, aryl phosphoranes, aryl alkyl phosphoranes, N,N'-arylimidazolidin-2-iminyl, N-aryl-N'-alkylimidazolidin-2-iminyl wherein aryl is a $C_6$ to $C_{18}$ aromatic hydrocarbon, optionally having at least one substituent selected from $C_1$ to $C_6$ alkyl optionally substituted by at least one halogen, $C_1$ to $C_6$ alkoxy, halogen, cyano, nitro, or $SF_5$;

iii. -heteroaryl, —CO-heteroaryl, —(CO)—O-heteroaryl, sulfinyl heteroaryl, sulfonyl heteroaryl, -(P=O)-di-heteroaryl, phosphinyl diheteroaryl, phosphinyl arylheteroaryl, phosphinyl heteroaryl alkyl, phosphonyl heteroaryl, heteroaryl phosphoranes, heteroaryl aryl phosphoranes, heteroaryl aryl alkyl phosphoranes, N,N'-heteroarylimidazolidin-2-iminyl, N-heteroaryl-N'-alkylimidazolidin-2-iminyl, N-heteroaryl-N'-arylimidazolidin-2-iminyl wherein heteroaryl is a $C_2$ to $C_{18}$ heteroaromatic hydrocarbon, optionally having at least one substituent selected from $C_1$ to $C_6$ alkyl optionally substituted by at least one halogen, $C_1$ to $C_6$ alkoxy, halogen, cyano, nitro, or $SF_5$;

and

W is selected from hydrogen, halogen, a metal selected from Li, Na, K, Rb, Cs, Be, Mg, Ca, Sr, Ba Sc, Ti, V, Cr, Mn, Fe, Co, Ni, Cu, Zn, Y, Zr, Mo, Ru, Rh, Pd, Ag, Cd, W, Re, Os, Ir, Pt, Au, Hg, Al, Ga, In, Ge, Sn, Pb, As, Sb, Bi, Se, Te, La, Sm, Eu, Yb, U or a cationic organic group, a substituted borane $—BR^IR^{II}R^{III}$ or a substituted silicon $—SiR^IR^{II}R^{III}$, wherein $R^I$, $R^{II}$ and $R^{III}$ may be same or different and each stands for hydrogen, halogen, an optionally —O— bonded $C_1$ to $C_{20}$ straight chain, branched chain or cyclic aliphatic hydrocarbon, optionally having one or more unsaturated bonds or one or more hetero atoms in the chain, a $C_5$ to $C_{18}$ heteroaromatic hydrocarbon, a $C_6$ to $C_{18}$ aromatic hydrocarbon or partially arene-hydrogenated forms thereof, each hydrocarbon optionally being substituted by one or more groups selected from $C_1$ to $C_{20}$ straight chain, branched chain or cyclic aliphatic hydrocarbons, or one or more heterosubstituents.

2. Process according to claim 1, wherein the dimeric phosphazene-derived catalyst is represented by the following formula (III):

(III)

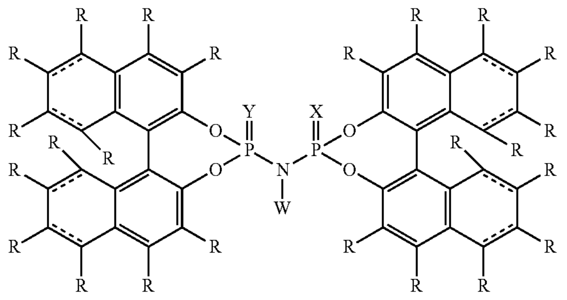

wherein the substituent R is the same or different on each position and is defined as in claim 1, X and Y have the meanings as defined in claim 1 and W represents hydrogen, an alkali metal or an earth alkaline metal.

3. Process according to claim 1, wherein the dimeric phosphazene-derived catalyst is represented by the following formula (IVa):

(IVa)

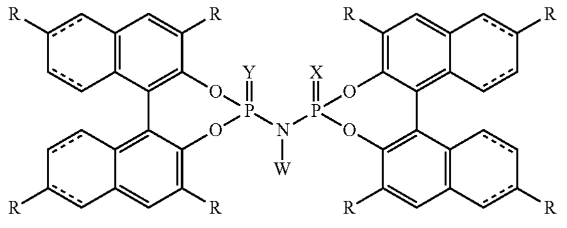

wherein the substituent R is the same or different on each position and is defined as in claim 1, X and Y have the meanings as defined in claim 1 and W represents hydrogen, an alkali metal or an earth alkaline metal.

4. Process according to claim 1, wherein the dimeric phosphazene-derived catalyst is represented by the following formula (IVb):

(IVb)

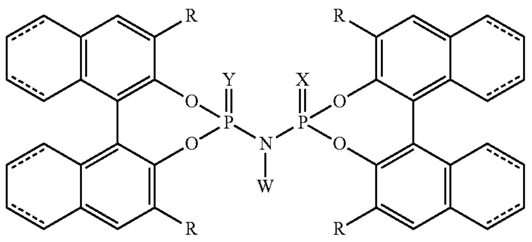

wherein the substituent R is the same or different on each position and is defined as in claim 1, X and Y have the meanings as defined in claim 1 and W represents hydrogen, an alkali metal or an earth alkaline metal.

5. Process according to claim 1, wherein the substituent R is the same or different on each position and represents halogen, a straight chain, branched chain or cyclic $C_1$ to $C_{20}$ aliphatic hydrocarbon or a $C_6$ to $C_{18}$ aromatic hydrocarbon, said aliphatic hydrocarbon and/or aromatic hydrocarbon being substituted by one or more halogens, $SF_5$, $NO_2$ or a straight chain, branched chain or cyclic $C_1$ to $C_{20}$ aliphatic hydrocarbon, being substituted by one or more halogens, $SF_5$, $NO_2$ on the aliphatic hydrocarbon.

6. Process according to claim 1, wherein Y is defined as O or $NR^N$ and X is defined as $NR^N$, wherein $R^N$ is an electron withdrawing or electron donating group, being the same or different on each position and being selected from:

i. sulfinyl alkyl or sulfonyl alkyl, wherein alkyl is a $C_1$ to $C_{20}$ straight chain, branched chain or cyclic aliphatic hydrocarbon, optionally having at least one substituent selected from $C_1$ to $C_6$ alkoxy, halogen, cyano, nitro or $SF_5$;

ii. sulfinyl aryl, or sulfonyl aryl, wherein aryl is a $C_6$ to $C_{18}$ aromatic hydrocarbon, optionally having at least one substituent selected from $C_1$ to $C_6$ alkyl optionally substituted by at least one halogen, $C_1$ to $C_6$ alkoxy, halogen, cyano, nitro or $SF_5$;

iii. sulfinyl heteroaryl, or sulfonyl heteroaryl, wherein heteroaryl is a $C_2$ to $C_{18}$ heteroaromatic hydrocarbon, optionally having at least one substituent selected from $C_1$ to $C_6$ alkyl optionally substituted by at least one halogen, $C_1$ to $C_6$ alkoxy, halogen, cyano, nitro or $SF_5$; and wherein R, $R^P$ and W have the meanings as defined in claim 1.

7. Process according to claim 1, wherein the substrate comprises a ratio of Neral and Geranial ranging from Neral (Z:E=>99:1) to Geranial (Z:E=<1:99).

8. Process according to claim 1, wherein the obtained reaction mixture is additionally subjected to a hydrogenation treatment whereby a reaction mixture containing at least one of menthol, isomenthol, neomenthol and neoisomenthol is obtained.

9. Process according to claim 1, wherein the obtained reaction mixture is further reacted with olivetol in the presence of a Lewis or Brønsted acid, whereby a reaction mixture containing THC and/or CBD is obtained.

10. A process for the asymmetric synthesis of isopiperitenol of formula (I), (I)

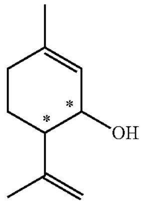

wherein a Neral-derivative of the formula (V)

(V)

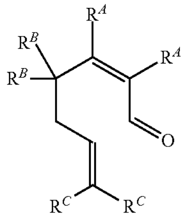

is cyclized in the presence of a dimeric phosphazene-derived catalyst of formula (II):

(II)

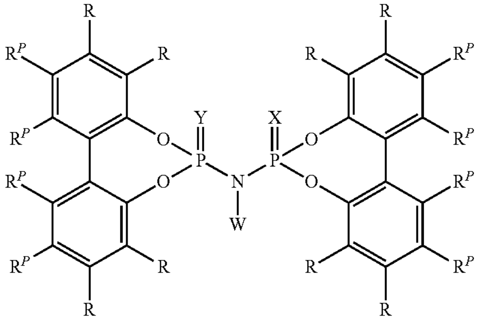

wherein in said formula (II):

R is the same or different on each position and is each selected from hydrogen, halogen, $SF_5$, $NO_2$, cyano, $C_1$ to $C_{20}$ straight chain, branched chain or cyclic aliphatic hydrocarbons, optionally having one or more halogens, $SF_5$, $NO_2$ or cyano on the aliphatic hydrocarbon, $C_6$ to $C_{18}$ aromatic hydrocarbons or $C_5$ to $C_{18}$ heteroaromatic hydrocarbons, each aromatic or heteroaromatic hydrocarbon optionally being substituted by one or more substituents selected from halogen, $SF_5$, $NO_2$, cyano, $C_1$ to $C_{20}$ straight chain, branched chain or cyclic aliphatic hydrocarbons, optionally having one or more halogens, $SF_5$, $NO_2$ or cyano on the aliphatic hydrocarbon, $R^P$ is the same or different on each position and has the meaning of R, or two $R^P$ on the same aryl ring may form a ring with each other which may be an aromatic ring structure or an aliphatic ring structure, which aromatic ring and/or aliphatic ring structure may be substituted with one or more substituents R, X and Y are the same or different and are either oxygen or $NR^N$; wherein:

$R^N$ is an electron withdrawing or electron donating group, being the same or different on each position and being selected from:

i. -alkyl, —CO-alkyl, —(CO)—O-alkyl, sulfinyl alkyl, sulfonyl alkyl, sulfonyl iminoalkyl, sulfonyl bisiminoalkyl, phosphinyl dialkyl, phosphonyl alkyl, alkyl phosphorane, N,N'-alkylimidazolidin-2-iminyl wherein alkyl is a $C_1$ to $C_{20}$ straight chain, branched chain or cyclic aliphatic hydrocarbon, optionally having at least one substituent selected from $C_1$ to $C_6$ alkoxy, halogen, cyano, nitro, or $SF_5$;

ii. -aryl, —CO-aryl, —(CO)—O-aryl, sulfinyl aryl, sulfonyl aryl, sulfonyl iminoaryl, sulfonyl iminosulfonylaryl, sulfonyl bisiminoaryl, phosphinyl diaryl, phosphinyl alkylaryl, phosphonyl aryl, aryl phosphoranes, aryl alkyl phosphoranes, N,N'-arylimidazolidin-2-iminyl, N-aryl-N'-alkylimidazolidin-2-iminyl wherein aryl is a $C_6$ to $C_{18}$ aromatic hydrocarbon, optionally having at least one substituent selected from $C_1$ to $C_6$ alkyl optionally substituted by at least one halogen, $C_1$ to $C_6$ alkoxy, halogen, cyano, nitro, or $SF_5$;

iii. -heteroaryl, —CO-heteroaryl, —(CO)—O-heteroaryl, sulfinyl heteroaryl, sulfonyl heteroaryl, -(P=O)-di-heteroaryl, phosphinyl diheteroaryl, phosphinyl arylheteroaryl, phosphinyl heteroaryl alkyl, phosphonyl heteroaryl, heteroaryl phosphoranes, heteroaryl aryl phosphoranes, heteroaryl aryl alkyl phosphoranes, N,N'-heteroarylimidazolidin-2-iminyl, N-heteroaryl-N'-alkylimidazolidin-2-iminyl, N-heteroaryl-N'-arylimidazolidin-2-iminyl wherein heteroaryl is a $C_2$ to $C_{18}$ heteroaromatic hydrocarbon, optionally having at least one substituent selected from $C_1$ to $C_6$ alkyl optionally substituted by at least one halogen, $C_1$ to $C_6$ alkoxy, halogen, cyano, nitro, or $SF_5$;

and

W is selected from hydrogen, halogen, a metal selected from Li, Na, K, Rb, Cs, Be, Mg, Ca, Sr, Ba Sc, Ti, V, Cr, Mn, Fe, Co, Ni, Cu, Zn, Y, Zr, Mo, Ru, Rh, Pd, Ag, Cd, W, Re, Os, Ir, Pt, Au, Hg, Al, Ga, In, Ge, Sn, Pb, As, Sb, Bi, Se, Te, La, Sm, Eu, Yb, U or a cationic organic group, a substituted borane $—BR^IR^{II}R^{III}$ or a substituted silicon $—SiR^IR^{II}R^{III}$, wherein $R^I$, $R^{II}$ and $R^{III}$ may be same or different and each stands for hydrogen, halogen, an optionally —O— bonded $C_1$ to $C_{20}$ straight chain, branched chain or cyclic aliphatic hydrocarbon, optionally having one or more unsaturated bonds or one or more hetero atoms in the chain, a $C_5$ to $C_{18}$ heteroaromatic hydrocarbon, a $C_6$ to $C_{18}$ aromatic hydrocarbon or partially arene-hydrogenated forms thereof, each hydrocarbon optionally being substituted by one or more groups selected from $C_1$ to $C_{20}$ straight chain, branched chain or cyclic aliphatic hydrocarbons, or one or more heterosubstituents, and the reaction mixture is further reacted, in the presence of a Lewis or Brønsted acid with a resorcin-derived compound of the formula (VI)

(VI)

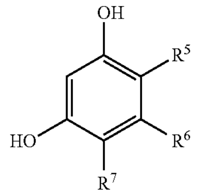

whereby a reaction mixture containing racemic or optically active CBD- and/or THC-derivatives of the general formula (VIIa) and (VIIb) is obtained;

(VIIa)

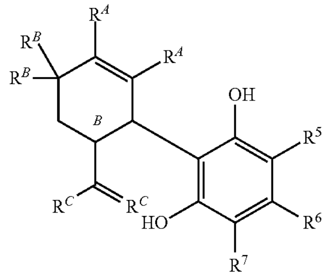

(VIIb)

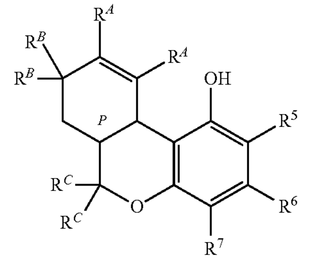

wherein $R^A$ is, independently from each other, the same or different and is each hydrogen, a $C_1$ to $C_6$ alkyl group, $—CH_2OH$, or $—COOR^e$ with Re being H or a $C_1$ to $C_6$ alkyl group;

$R^B$ is, independently from each other, the same or different and is each hydrogen, a $C_1$ to $C_6$ alkyl group, or two of $R^B$ or two of $R^C$, respectively, may form a ring amongst each other, $R^C$ is, independently from each other, the same or different and is each a $C_1$ to $C_6$ alkyl group, or two of $R^B$ or two of $R^C$, respectively, may form a ring amongst each other, $R^5$ and $R^7$ are, independently from each other, the same or different and are each hydrogen or $—COOR^e$ with Re being H or a $C_1$ to $C_6$ alkyl group;

$R^6$ represents hydroxy, a $C_1$ to $C_{12}$ alkyl group, optionally being further substituted by one or more hydroxyl groups.

11. A process according to claim 1, wherein the dimeric phosphazene-derived catalyst, wherein R, $R^P$, Y, X and W are as defined in claim 1, is bound to a solid support, optionally through a linker;

wherein the linker is an aliphatic, heteroaliphatic, aromatic or heteroaromatic hydrocarbon group, each hydrocarbon group optionally being further substituted by one or more heterosubstituents, aliphatic, heteroaliphatic, aromatic or heteroaromatic hydrocarbon groups, each hydrocarbon group optionally being substituted by one or more heterosubstituents; and wherein the solid support is insoluble in the reaction mixture and is selected from wool, cotton, polystyrene, polysiloxane, polyacrylate, polyethylene, polypropylene, polyethylene glycol and polyamide, and copolymers thereof, each optionally having at least one halogen, hydroxy, sulfonyl, alkoxy, halogen-substituted alkoxy on the aliphatic hydrocarbon or oxygen in the aliphatic hydrocarbon chain.

12. A process according to claim 11, wherein the dimeric phosphazene-derived catalyst is bound to a solid support via a linker between the solid support and an aromatic or cycloaliphatic backbone of the dimeric phosphazene-derived catalyst, Y and X are defined as oxygen or $NR^N$, $R^N$ is defined as in claim 1, R and $R^P$ are as defined in claim 1.

13. A process according to claim 11, wherein the dimeric phosphazene-based catalyst is bound to a solid support via linker between an $NR^N$ substituent and the solid support, wherein the linker and the solid support are as defined in claim 10 and, in the dimeric phosphazene-derived catalyst Y is oxygen or $NR^N$, X is $NR^N$, $R^N$ is a straight or branched alkyl chain or a polyether alkyl chain, said alkyl chain having at least one halogen.

* * * * *